(12) United States Patent
Adams

(10) Patent No.: US 7,263,777 B2
(45) Date of Patent: Sep. 4, 2007

(54) PANEL SCRIBING DEVICE

(75) Inventor: Jerome T. Adams, Hockessin, DE (US)

(73) Assignee: E. I. de Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/154,487

(22) Filed: Jun. 16, 2005

(65) Prior Publication Data

US 2006/0042724 A1    Mar. 2, 2006

Related U.S. Application Data

(60) Provisional application No. 60/601,676, filed on Aug. 13, 2004.

(51) Int. Cl.
 *B43L 13/00* (2006.01)
 *B31B 1/25* (2006.01)

(52) U.S. Cl. .......................................... 33/32.6; 83/879

(58) Field of Classification Search ................. 225/94, 225/96, 103–105, 1, 2, 4; 144/253.1–253.9, 144/253.91, 286.1, 286.5; 83/452, 859, 453–456, 83/879–881, 490; 73/78, 81–85; 33/18.1, 33/20.1, 32.1–32.3, 32.5–32.6
See application file for complete search history.

(56) References Cited

U.S. PATENT DOCUMENTS 2,252,535 A  *  8/1941  West et al. .................... 33/445
2,957,244 A  *  10/1960 Brewer et al. ................ 33/32.3
3,881,255 A  *  5/1975  Pantek ....................... 33/27.01
4,224,854 A  *  9/1980  Malacheski et al. .......... 83/745
4,228,937 A     10/1980 Tocci
4,524,894 A  *  6/1985  Leblond ......................... 225/2
5,767,423 A     6/1998  Camp et al.
6,567,541 B1    5/2003  Van et al.
6,604,420 B2    8/2003  Hawbaker et al.

FOREIGN PATENT DOCUMENTS

| BR | 9103302 | 3/1993 |
| CA | 962853  | 2/1975 |
| DE | 2428687 | 11/1975 |
| SU | 634179  | 11/1978 |

* cited by examiner

*Primary Examiner*—Kenneth E. Peterson
*Assistant Examiner*—Phong Nguyen
(74) *Attorney, Agent, or Firm*—Sudhir G. Deshmukh

(57) ABSTRACT

An apparatus for scribing the coating on a coated panel; comprising a base, at least one linear guide affixed to the base, a moveable table, a pivotable bracket mounted on the base, a cutter element mounted on the bracket; a loading mechanism positioned on top of the bracket, such that when the cutter element in the cutter assembly is brought into contact with a panel positioned on the moveable table, the loading mechanism applies a uniform force to the panel position on the table. The cutter element in contact with the panel scribes the panel through the coating thereby forming a scribe of at least one line on the panel.

6 Claims, 3 Drawing Sheets

PANEL SCRIBING DEVICE

CROSS-REFERENCE TO RELATED APPLICATION

This application claims priority under 35 U.S.C. §119 from U.S. Provisional Application Ser. No. 60/601,676, filed Aug. 13, 2004.

BACKGROUND OF THE INVENTION (1) Field of the Invention

This invention relates to an apparatus that uniformly scribes a coated panel for adhesion testing purposes.

(2) Description of Related Art

A wide variety of substrates are coated with single and often multiple layers of clear and/or pigmented coating compositions. The adhesion of the coating composition to the substrate is of concern and adhesion measurements by various methods have been developed and are in current commercial use. In one particularly useful adhesion test, an area of the coating on a panel is scribed through to the substrate and tape is applied over the scribed area. The tape is removed and the amount of the coating that has been removed is determined and the adhesion of the coating to the substrate can be rated. This makes it possible to compare the adhesion of various coatings. ASTM D3359 describes this adhesion test that is conventionally used.

The problem with this test and related tests is the scribing of the coating through to the substrate. There are a variety of hand held cutting devices available to scribe a coating, in particular, to scribe a pattern in the coating, for example, a crosshatch pattern on the coated substrate which usually is a test panel. With such hand held devices, operator variability, operator error and/or dull cutting edges on the device result in non-uniform and non-replicable scribing of the coating. For example, the scribed pattern applied by different operators depends on the pressure applied by the operator thereby varying the depth of the scribe. Also, on how steady the scribing tool is held by an operator can affect the width of the scribe and the sharpness or dullness of the cutting tool also will affect the scribe. Operator fatigue and long term muscular damage that can be caused by repeated scribing by an operator day after day has also been a problem.

There is a need for an apparatus that can rapidly scribe substrates in comparison to hand scribing, can easily be operated by a person with minimal effort without causing fatigue or physical injury to a person and the apparatus has to be safe, for example, from pinch points, must be ergonomically acceptable and must produce uniform and repeatable scribes or scribe patterns on a coated substrate. Every scribe or scribe pattern formed must penetrate the coating through to the substrate and must be uniform and repeatable. The novel apparatus of this invention accomplishes the above.

SUMMARY OF THE INVENTION

The invention is directed to an apparatus for scribing the coating on a coated panel; wherein the apparatus comprises the following:

a base, at least one linear guide affixed to the base, a moveable table positioned on the at least one linear guide and the base, a pivotable bracket mounted on the base, a cutter assembly of a cutter element and a holder for the cutter element where the cutter assembly is mounted on the bracket and wherein the cutter element is in a substantially parallel relationship to the table;

a loading mechanism positioned on top of the bracket, such that when the cutter element in the cutter assembly is brought into contact with a panel positioned on the moveable table, the loading mechanism applies a uniform force to the panel position on the table;

a stopping means attached to the moveable table to prevent the panel from moving during scribing and means for moving the table positioned on the base and in contact with the linear guide on the base such that when the table is moved on the guide by the means for moving the table, the cutter element in contact with the panel scribes the panel through the coating thereby forming a scribe of at least one line on the panel.

DETAILED DESCRIPTION OF THE EMBODIMENTS

The novel apparatus of this invention is used to scribe painted or coated panels, usually metal panels, primarily to determine the level adhesion of the paint or coating to the metal substrate and also to determine the level of adhesion of a coating after it has been exposed to moisture conditions, such as high humidity. Scribed coated metal panels can also be tested for corrosion resistance wherein a scribed coated panel is subjected to salt spray for a period of time and then the amount the coating that is eroded from the scribe mark is measured.

To provide accurate test results, the scribes in the coated panels must be uniform and this cannot be accomplished by conventional hand scribing a coated panel with a knife, cutter device or other sharp objects. The human factors from operator to operator vary widely and hence, test results are not accurate. In the novel apparatus of this invention, a coated or painted panel is held in position on a moveable table of the apparatus and then scribed by moving moveable table beneath a cutter assembly having at least one sharp point or edge but generally has a row of sharp points, usually 6 sharp points, and is under pressure, usually provided by weights positioned over the cutter assembly thereby scribing the coating through to the substrate of the panel, usually a metal panel. Then the panel can be subjected to a variety of tests to determine coating adhesion, corrosion resistance of the coating and other properties.

The advantages of the novel apparatus are many. The apparatus is easily operated because of the leverage provided by the movable lever assembly that moves the table having the panel positioned thereon, thereby making the apparatus ergonomically acceptable. The apparatus is safe to operate since pinch points and edges have been removed or shielded. Uniform pressure is applied to the cutter element thereby providing straight line scribes of an even depth and the depths of the scribes can be adjusted by the addition or subtraction of weights positioned over the cutter element. Panels can be positioned at a variety of angles on the table and patterns from squares to diamond shapes can be made. Panels are held in place without the need to attach or hold down the panel while cutting. Panels of different thickness and size can be scribed without adjustment. Any size panel that fits on the table can be scribed. Spacing between scribes and number of scribes can be changed quickly by using a different commercial cutter or custom cutter with a different number of points and spacing. Operation is simple and intuitive which reduces training of operators and maintenance of the apparatus. Panels can be easily loaded, positioned and removed with the cover held fixed in the raised position. Panels can be positioned to be scribed at any point within the cutter's reach. Track and "V" groove wheels self-align the table to be parallel with the cutter points.

Figure 1:
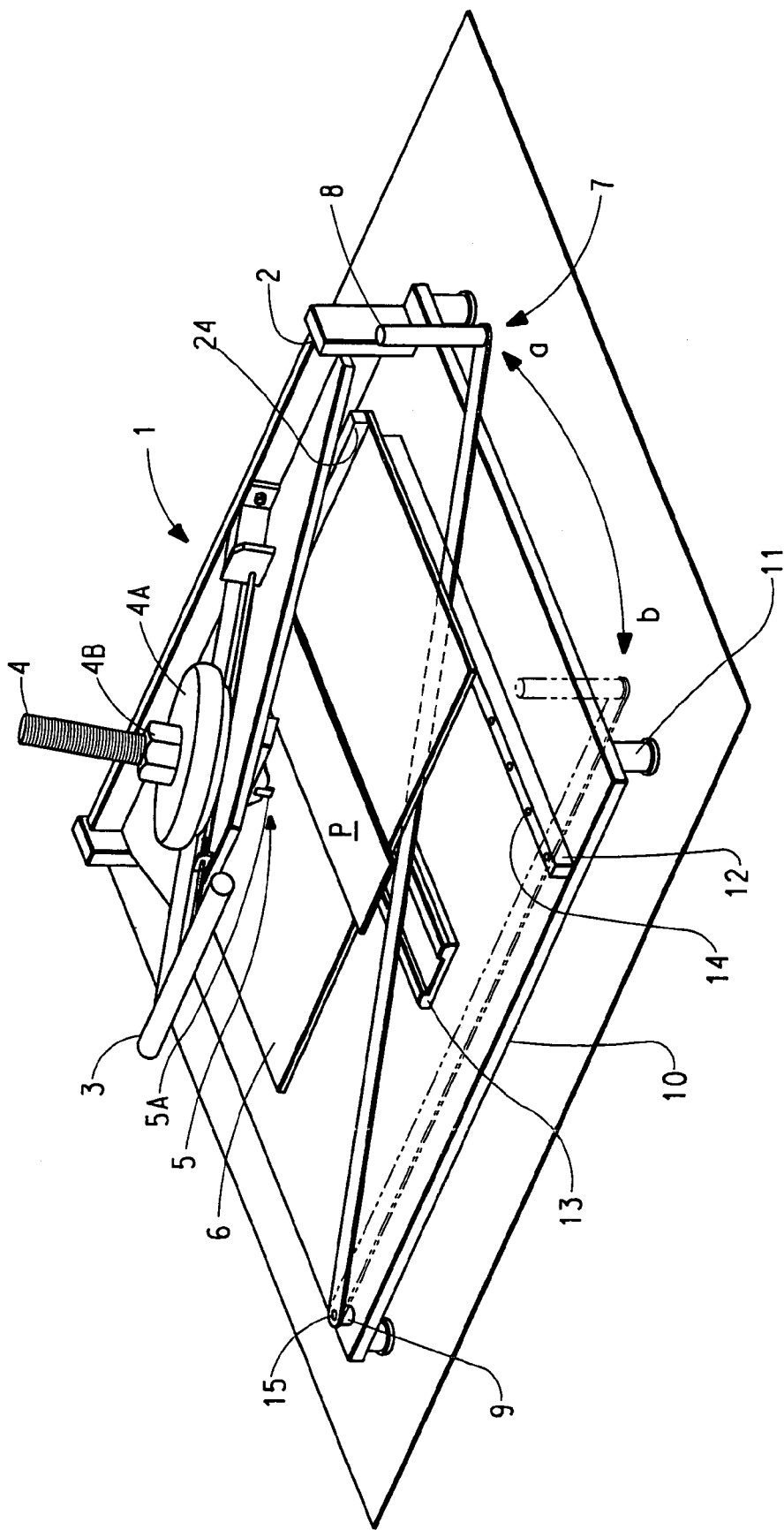
FIG. 1 shows a perspective view of the scribing apparatus of this invention.
Figure 4A:
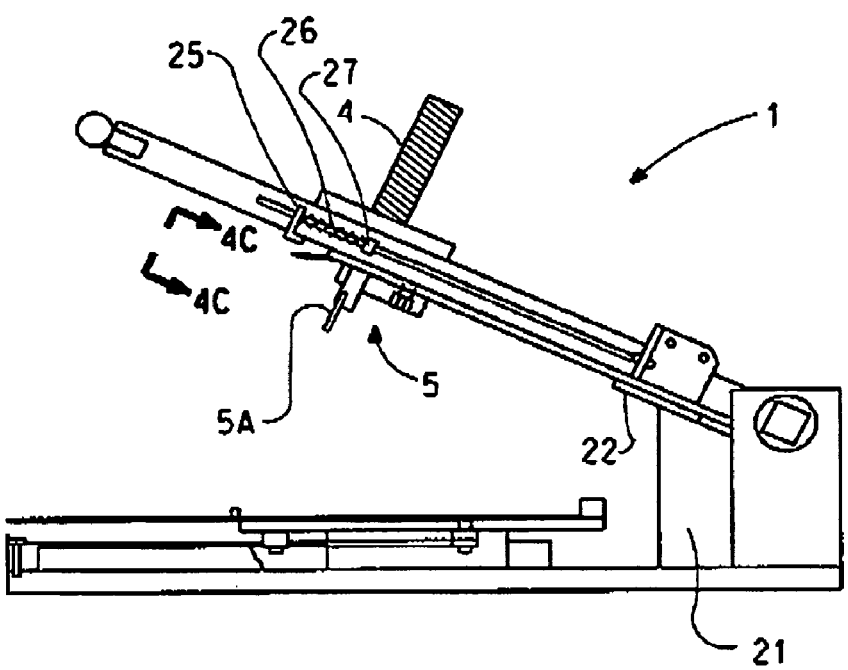
FIGS. 4A and 4B show side views of the scribing apparatus with the moveable table assembly in an open position and in an engaged position.
Figure 4B:
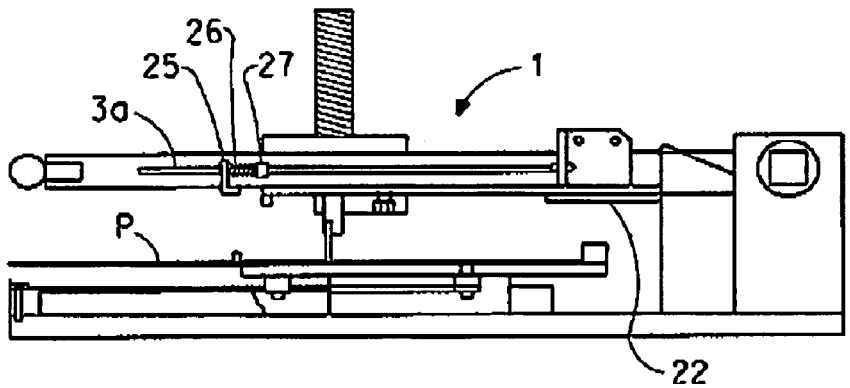
Figure 4C:
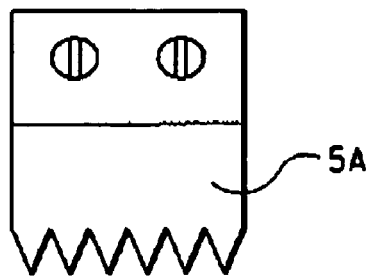
FIG. 4C shows a magnified view of a cutter element positioned in a cutter assembly.

FIG. 1 shows a perspective view of the apparatus. The apparatus has a moveable cover assembly (1) hinged at the back with hinge (2) and handle assembly (3) which allows for opening and closing by en operator. The cover assembly (1) has a threaded rod (4) attached thereto onto which weights (4A) are added to provide the desired test load conditions. Nut (4B) threaded onto the rod (4) holds the weights in place during operation of the apparatus. A cutter assembly (5) is attached to the under side of the cover assembly (1) with screws (not shown) and has a cutter element (5A) having a single row of sharp points, typically 6 sharp points. Typically, cutter elements are available from BYK Gardner, Columbia, Md. FIG. 4C shows a magnified view of cutter element 5A having six sham points.

A moveable table (6) is attached to movable lever assembly (7) and rests on centering rail (13) attached to base plate (10). A "V" grove wheel plate (not shown) is mounted on the underside of the moveable table (6) to guide it as it is being moved during scribing of the coating on a panel. Rail (12) is attached to the base plate (10) by screws (14) and lever assembly (7) rests thereon. A test panel (P) is positioned on movable table (6) and rests against panel stop (24) which prevents the test panel (P) from moving during scribing of the coating. There are four level adjustment screws (11) attached to the base plate (10) in each corner are used to level the apparatus. The moveable lever assembly (7) having handle (8) attached thereto is attached to a pivot post (9) attached to the base plate (10) with a screw (15) and is positioned under the moveable table (6). When the movable lever assembly (7) is moved from position (a) to position (b) thereby moving table (6) to scribe the coating on a test panel (P). Lever assembly (7) is shown by broken lines in position (b).

Figure 2:
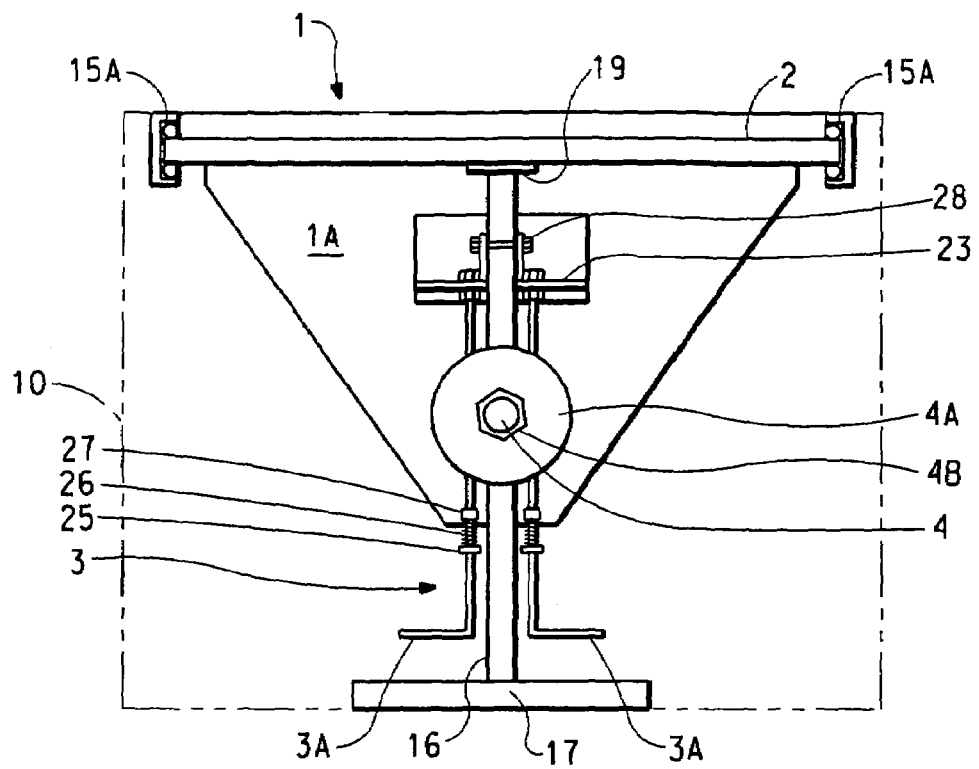
FIG. 2 shows the top plan view of the apparatus.

FIG. 2 shows the top plan view of the apparatus. The hinge (2) is attached to panel (1A) of the cover assembly (1) and moveably positioned in two bearing assemblies (15A) that are attached to the base plate (10) to allow the cover assembly to open and close. Handle assembly (3) is attached to plate (19) that is attached to the hinge (2) which is attached to top of the panel (1A). Rod (16) of the handle assembly is attached to plate (19) and to fixed handle (17). The threaded rod (4) is attached to rod (16) on which weights (4A) are held in place by nut (4B). Moveable handles (3A) are attached handle assembly (3) by a bracket (25) and bolt (28) which slides on rod (16). Compressible springs (26) are compressed by a collar having a set screw (27) when moveable handles (3A) are engaged by an operator and pulled toward fixed handle (17) thereby allowing the cover assembly to lower and to engage the cutter element (5A) of the cutter assembly (5) shown in FIG. 1 to contact test panel P. Bolt (28) attaches bracket (23) to rod (16). FIGS. 4A and 4B, described hereinafter, show in detail the mechanism involved in opening and closing the cover assembly (1).

Figure 3:
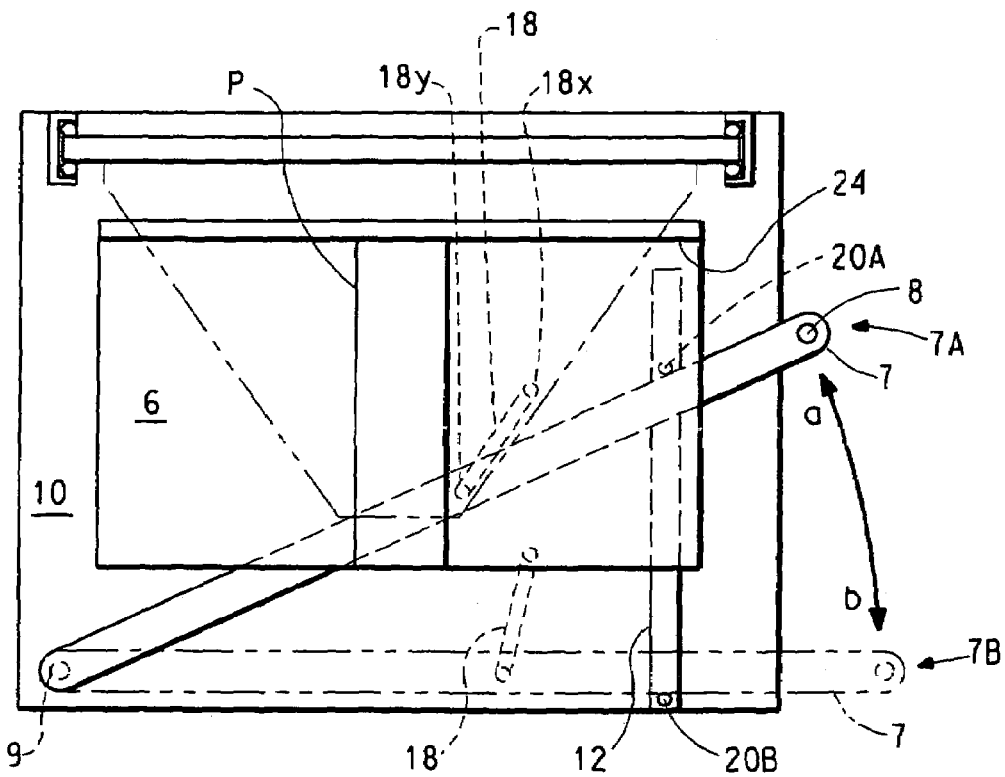
FIG. 3 shows a top plan view of the apparatus elements of the table guide and lever assembly in two positions.

FIG. 3 shows a top plan view of the apparatus showing the movable lever assembly (7) for moving the moveable table (6) between two positions (a) and (b) shown in dashed lines. The movable lever assembly (7) is attached to pivot (9) that is attached to the base plate (10). Connecting rod (18) is attached to the lever assembly at point (y) and to the moveable table (6) at point (x). The positions (a) and (b) of the moveable lever assembly (7) are shown in dashed lines. A test panel (P) is placed on the moveable table (6) in center of the table and against panel stop (24). The cover assembly (1) is lowered into the closed position so that the cutters of the cutter assembly (5) engage the test panel (P) as shown in FIG. 4B. The lever assembly (7) is moved by an operator from position (a) to (b) by grasping and pulling the handle (8) of the lever assembly (7). The lever assembly is shown as 7A in position (a) and 7B in position (b). As the operator moves the lever assembly (7) from stop (20A) to stop (20)B on rail (12), the moveable table (6) positioned on rail (13), shown in FIG. 1, is moved thereby scribing the test panel (P) with the cutter element (5A), shown in FIG. 1. Then, the cover assembly (1), shown in FIG. 1, is opened by the operator disengaging the moveable handles (3A) and the cover assembly (1) is returned to its open position. The panel is repositioned, generally 90 degrees from its first position, and the panel is scribed a second time to provide the desired scribe pattern.

FIGS. 4A and 4B shows side views of the scribing apparatus in the open position and in the engaged position. In FIG. 4A, the cover assembly (1) is in the open position showing the cutter assembly (5) and cutter element (5A). In FIG. 4B, the cover assembly (1) is in the closed position with the cutter element (5A) in engagement with the test panel (P). In FIG. 4A, post (21) is in engagement with spring actuated slide (22) which maintains the cover assembly (1) in the open position. By an operator pulling handles (3A) of the handle assembly (3), shown in FIG. 2, the slide (22) actuated by springs (26), is disengaged from the post (21) and the cover assembly (1) and is allowed to close as posts (21) fit through plate (1A). Weights (not shown) can be mounted on the threaded rod (4) to provide the desired pressure to the cutter element (5A) for scribing the test panel.

The following example illustrates the operation and advantages of the novel apparatus of this invention.

EXAMPLE

Eleven panels were prepared by applying a base coat lacquer over electrocoated primed phosphated steel panel and then a urethane clear coat was applied over the base coat and the panels were dried. Each of the panels was scribed with the novel scribing apparatus of this invention using 2 mm spaced cutter forming a square grid having 25 squares. Each horizontal line in the grid has 5 segments and each vertical line has 5 segments. Each of the panels were hand scribed by the same operator in a different position on each of the panels using a SAR-8603 BYK Gardner cutting device using 2 mm spacing forming square grid having 25 squares. The panels were then held at 75° F. (24° C.) for 7 days to fully cure coating and each of the grids was examined under a 10× hand lens to determine if each segment was cut through to the metal substrate. If not cut through to the substrate, a defect was recorded in the following table:

TABLE

| Panel Number | Invention Scribing Device % defects | Hand Cut % defects |
|---|---|---|
| 1 | 0.0 | 0.0 |
| 2 | 0.0 | 8.3 |
| 3 | 0.0 | 0.0 |
| 4 | 0.0 | 11.7 |
| 5 | 8.3 | 0.0 |
| 6 | 3.3 | 3.3 |
| 7 | 0.0 | 0.0 |
| 8 | 0.0 | 15.0 |
| 9 | 0.0 | 18.3 |
| 10 | 0.0 | 0.0 |
| 11 | 0.0 | 6.7 |
| Average % defective | 1.1 | 5.8 |

The data in the above table shows that there are substantially more defective segments (not cut through to the metal) using the hand-scribing device in comparison to the novel scribing apparatus of this invention.

The invention claimed is:

1. An apparatus for scribing a coating on a coated panel; wherein the apparatus comprises the following:
   a base,
   at least one linear guide affixed to said base,
   a moveable table positioned on the at least one linear guide and base,
   a pivotable bracket mounted on said base,
   a cutter assembly comprising a cutter element and a holder for said cutter element where said cutter assembly is mounted on the bracket and wherein said cutter element is in a substantially perpendicular relationship to said table;
   a handle and spring means attached to the pivotable bracket for allowing the lowering and raising of the pivotable bracket thereby engaging and disengaging the cutter assembly with the coated panel;
   a loading mechanism positioned on top of said bracket, such that when said cutter element in the cutter assembly is brought into contact with a panel positioned on said moveable table, said loading mechanism applies a uniform force to the panel position on said table;
   a stopping means attached to the moveable table to prevent the panel from moving during scribing; and
   means for moving said table comprising a lever pivotably attached to said table and said base and in contact with said linear guide on said base such that when said table is moved on said guide by said means for moving said table, said cutter element in contact with the panel scribes the panel through the coating thereby forming a scribe of at least one line on the panel and wherein said lever has a handle to thereby allow manual movement of said table to scribe the coating on the panel.

2. The apparatus of claim 1 wherein said cutter device comprises a multiplicity of cutting edges that scribe a multiplicity of lines on the panel.

3. The apparatus of claim 1 wherein the pivotable bracket has a handle attached thereto to allow manual engagement of cutter device with the coated panel.

4. The apparatus of claim 1 wherein the stopping means comprises a bar attached to the moveable table.

5. The apparatus of claim 1 wherein the loading mechanism comprises weights positioned on the bracket and held in place by mechanical means.

6. A method of scribing a coating of a coated panel which comprises positioning a panel on the table of the device of claim 1 bringing the cutter device in contact with the panel and moving the table to scribe said panel.

* * * * *